United States Patent [19]
Allais et al.

[11] 4,147,790
[45] Apr. 3, 1979

[54] (4-PHENYL-PIPERAZINO ALKYL)-3-BENZOYL-BENZENE ALKANOATES

[75] Inventors: André Allais, Gagny; François Clémence, Paris; Roger Deraedt, Pavillons-sous-Bois, all of France

[73] Assignee: Roussel Uclaf, Paris, France

[21] Appl. No.: 869,361

[22] Filed: Jan. 13, 1978

[30] Foreign Application Priority Data

Jan. 21, 1977 [FR] France ................ 77 01712
Oct. 17, 1977 [FR] France ................ 77 31164

[51] Int. Cl.² ............... A61K 31/495; C07D 295/14
[52] U.S. Cl. ................................ 424/250; 544/394
[58] Field of Search ................. 544/394; 424/250

[56] References Cited
U.S. PATENT DOCUMENTS
3,931,302  1/1976  Allais et al. ................ 260/517

Primary Examiner—Jose Tovar
Attorney, Agent, or Firm—Hammond & Littell

[57] ABSTRACT

Benzophenones of the formula

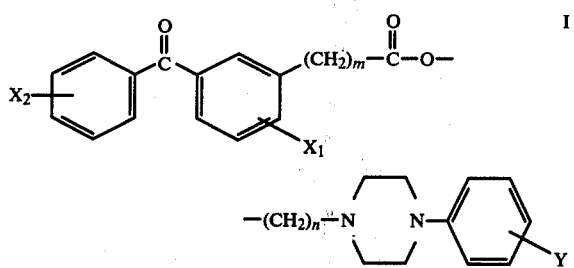

wherein $X_1$ is selected from the group consisting of hydrogen and alkyl of 1 to 5 carbon atoms, $X_2$ is selected from the group consisting of hydrogen, halogen and alkoxy of 1 to 5 carbon atoms, m is a whole number from 1 to 10, n is a whole number from 2 to 5 and Y is in the 2,3 or 4-position and is selected from the group consisting of hydrogen, halogen, $CF_3-$, $CF_3O-$, $CF_3S-$, alkyl of 1 to 8 carbon atoms and alkoxy of 1 to 8 carbon atoms and their non-toxic, pharmaceutically acceptable acid addition salts having analgesic activity and their preparation.

19 Claims, No Drawings

(4-PHENYL-PIPERAZINO ALKYL)-3-BENZOYL-BENZENE ALKANOATES

STATE OF THE ART

U.S. Pat. No. 3,931,302 and Belgium Pat. No. 824,658 describe the free benzophenone acids of formula I and simple esters thereof very different from the esters of formula I.

OBJECTS OF THE INVENTION

It is an object of the invention to provide the novel esters of formula I and their non-toxic, pharmaceutically acceptable acid addition salts and a novel process for their preparation.

It is another object of the invention to provide novel analgesic compositions and to provide a novel method of relieving pain in warm-blooded animals.

These and other objects and advantages will become obvious from the following detailed description.

THE INVENTION

The novel benzophenone of the invention are selected from the group consisting of compounds of the formula

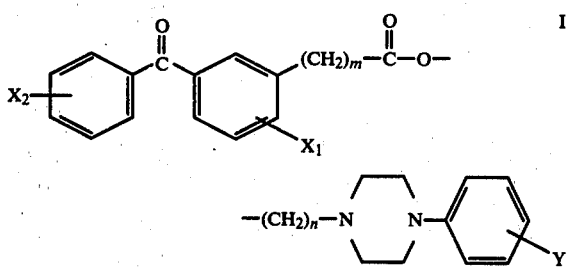

wherein $X_1$ is selected from the group consisting of hydrogen and alkyl of 1 to 5 carbon atoms, $X_2$ is selected from the group consisting of hydrogen, halogen and alkoxy of 1 to 5 carbon atoms, m is a whole number from 1 to 10, n is a whole number from 2 to 5 and Y is in the 2,3 or 4-position and is selected from the group consisting of hydrogen, halogen, $CF_3-$, $CF_3O-$, $CF_3S-$, alkyl of 1 to 8 carbon atoms and alkoxy of 1 to 8 carbon atoms and their non-toxic, pharmaceutically acceptable acid addition salts.

In the compounds of formula I, $X_1$ and $X_2$ may be in any position on the benzene ring. When $X_1$ or Y is alkyl, they are preferably methyl or ethyl. When $X_2$ or Y is halogen, they are preferably chlorine or fluorine. When $X_2$ or Y is alkoxy, they are preferably methoxy or ethoxy. m is preferably 1,2,3,4,5 or 6 and n is preferably 2,3 or 4.

Examples of suitable acids for the formation of the acid addition salts are inorganic acids such as hydrochloric acid, hydrobromic acid, sulfuric acid or phosphoric acid, organic acids such as acetic acid, propionic acid, citric acid, oxalic acid or glyoxylic acid and sulfonic acids such as methane sulfonic acid or p-toluene sulfonic acid.

Among the preferred compounds of formula I are those wherein $X_2$ is hydrogen, those wherein $X_2$ is halogen, especially chlorine, those wherein $X_1$ is hydrogen, those wherein $X_1$ is alkyl of 1 to 5 carbon atoms, especially methyl, those wherein m is 1, those wherein n is 2 and those wherein Y is trifluoromethyl and their non-toxic, pharmaceutically acceptable acid addition salts.

Specific preferred compounds of formula I are 2-[4-(3-trifluoromethylphenyl)-1-piperazinyl]-ethyl 3-(4-chlorobenzoyl)-2-methyl-benzene-acetate, 2-[4-(3-trifluoromethylphenyl)-1-piperazinyl]-ethyl3-(4-chlorobenzoyl)-benzeneacetate, 2-[4-(3-trifluoromethylphenyl)-1-piperazinyl]-ethyl 3-(4-chlorobenzoyl)-2-methyl-benzenehexanoate and 2-[4-(4-chlorophenyl)-1-piperazinyl]-ethyl 3-(4-chlorobenzoyl)-benzeneacetate and their non-toxic, pharmaceutically acceptable acid addition salts, especially their hydrochlorides.

The novel process of the invention for the preparation of the compounds of formula I comprises reacting an acid of the formula

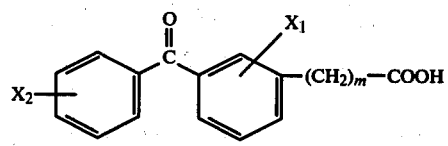

wherein $X_1$, $X_2$ and m have the above definition or a functional derivative thereof with an alcohol of the formula

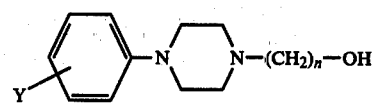

wherein Y and n have the above definition and optionally reacting the ester of formula I with a non-toxic, pharmaceutically acceptable acid to form the salt thereof.

In a preferred mode of the process of the invention, the functional derivative of the acid of formula II is an alkyl ester of 1 to 8 carbon atoms. The transesterification is effected in the presence of an alkaline agent such as an alkali metal hydride like sodium hydride, or alkali metal amide like sodium amide or potassium amide or an alkali metal alcoholate like sodium ethylate. The reaction is preferably effected in an organic solvent at 50° to 200° C.

Also useful in the process of the invention are the acid chlorides of the acids of formula II, especially

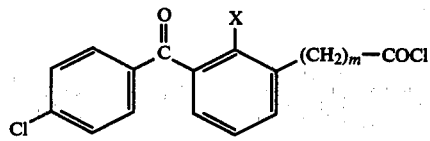

wherein X is hydrogen or methyl and m is 1 or 5 when reacted with an alcohol of the formula

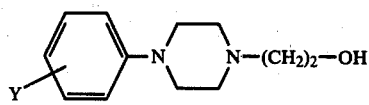

wherein Y is 4-chloro or 3-$CF_3$ when X is hydrogen and m is 1 or 3-$CF_3$ when X is methyl and m is 5.

The compounds of formula II and their functional derivatives are generally known and may be prepared by the process of French Pat. No. 2,085,638, for example. The alcohols of formula III are also known and may be prepared by the process of French Pat. No. 2,141,526, for example.

The novel analgesic compositions of the invention are comprised of an analgesically effective amount of at least one compound of formula I and its non-toxic, pharmaceutically acceptable acid addition salts and an inert pharmaceutical carrier or excipient. The compositions may be in the form of tablets, dragees, gelules, granules, suppositories, injectable solutions or suspensions, pomades, cremes, gels and aerosol preparations prepared in the usual manner.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers or preservatives.

The compositions of the invention have a remarkable analgesic activity while being practically devoid of toxicity. They are, therefore, useful for the treatment of muscular, articular or nervous pain, dental pain and migraines.

Among the preferred compositions are those containing 2-[4-(3-trifluoromethylphenyl)-1-piperazinyl]-ethyl 3-(4-chlorobenzoyl)-2-methyl-benzeneacetate, 2-[4-(3-trifluoromethylphenyl)-1-piperazinyl]-ethyl 3-(4-chlorobenzoyl)-benzene acetate, 2-[4-(3-trifluoromethylphenyl)-1-piperazinyl]-ethyl 3-(4-chlorobenzoyl)-2-methyl-benzenehexanoate and 2-[4-(4-chlorophenyl)-1-piperazinyl]-ethyl 3-(4-chlorobenzoyl)-benzeneacetate and their non-toxic, pharmaceutically acceptable acid addition salts.

The novel method of the invention for relieving pain in warm-blooded animals, including humans, comprises administering to warm-blooded animals an analgesically effective amount of at least one compound of formula I and their non-toxic, pharmaceutically acceptable acid addition salts. The compounds may be administered orally, rectally, parenterally or locally by topical application to skin and mucous. The usual daily dose of the compounds may be 0,4 to 40 mg/kg depending on the method of administration and the specific compound.

In the following examples there are described several preferred embodiments to illustrate the invention. However, it should be understood that the invention is not intended to be limited to the specific embodiments.

EXAMPLE 1

2-[4-(3-trifluoromethylphenyl)-1-piperazinyl]-ethyl 3-(4-chlorobenzoyl)-2-methyl-benzeneacetate hydrochloride A mixture of 6 g of methyl 3-(4-chlorobenzoyl)-2-methyl-benzeneacetate, 100 ml of anhydrous toluene and 7.1 g of (3-trifluoromethylphenyl)-piperazinyl-ethanol was refluxed for one hour while recycling toluene after passage through a column of siliporite and the mixture was allowed to become warm. 100 mg of a 50% suspension of sodium hydride in oil were added thereto and the mixture was refluxed for another 3 hours under the same conditions. The mixture was cooled and a few drops of acetic acid were added thereto. The mixture was evaporated to dryness under reduced pressure and the residue was taken up in anhydrous ether. The mixture was filtered and the filtrate was evaporated to dryness. The residue was dissolved in methylene chloride which was washed with water, dried and evaporated to dryness. The gummy residue was taken up in ether and alcoholic hydrochloric acid was added thereto. The mixture was filtered and the product was dried in an oven to obtain 2-[4-(3-trifluoromethylphenyl)-1-piperazinyl]-ethyl 3-(4-chlorobenzoyl)-2-methyl-benzeneacetate hydrochloride melting at 197° C.

Analysis: $C_{29}H_{29}Cl_2F_2N_2O_3$; molecular weight = 581.47; Calculated: %C 59.9; %H 5.02; %F 9.8; %Cl 12.19; %N 4.81; Found: 60.1; 5.2; 10.1; 12.2; 4.8.

EXAMPLE 2

2-[4-(3-trifluoromethylphenyl)-1-piperazinyl]-ethyl 3-(4-chlorobenzoyl)-benzeneacetate hydrochloride STEP A: 3-(4-chlorobenzoyl)-benzeneacetic acid chloride A solution of 8.235 g of 3-(4-chlorobenzoyl)-benzeneacetic acid in 20 ml of thionyl chloride was heated to reflux and then excess thionyl chloride was removed under reduced pressure. The residue was dissolved in benzene and the solution was evaporated to dryness under reduced pressure. The residue was dissolved in 50ml of anhydrous benzene to obtain a solution of 3-(4-chlorobenzoyl)-benzeneacetic acid chloride which was used as is for the next step.

STEP B: 2-[4-(3-trifluoromethylphenyl)-1-piperazinyl]-ethyl 3-(4-chlorobenzyl)-benzeneacetate hydrochloride 4.57 ml of anhydrous triethylamine were added to a solution of 8.22 g of 4-(3-trifluoromethylphenyl)-1-piperazinyl-ethanol in 80 ml of anhydrous benzene and the solution of Step A was added thereto. The reaction mixture was held at 20° C. for 19 hours and was then filtered. The filtrate was diluted with 100 ml of ether and the ether phase was washed with water, dried and filtered. The filtrate was evaporated to dryness and the gummy residue was dried under reduced pressure at 80° C. to obtain 15.98 g of raw 2-[4-(3-trifluoromethylphenyl)-1-piperazinyl]-ethyl 3-(4-chlorobenzoyl)-benzene-acetate in the form of a clear brown gum with an Rf = 0.25 (7–3 benzene-ethyl acetate eluant).

The said product was dissolved in 30 ml of ethanol and 4.28 ml of an anhydrous ethanolic 7N hydrochloric acid were added thereto with stirring. Anhydrous ether was added and the mixture stood overnight with icing and was then vacuum filtered. The product was washed with anhydrous ether and was dried at 60° C. under reduced pressure to obtain 14.18 g of raw product. The latter was washed with 100 ml of water at 20° C. and was vacuum filtered, washed and dried at 100° C. under reduced pressure to obtain 2-[4-(3-trifluoromethylphenyl)-1-piperazinyl]-ethyl 3-(4-chlorobenzoyl)-benzeneacetate hydrochloride melting at 136° C.

EXAMPLE 3

2-[4-(3-trifluoromethylphenyl)-1-piperazinyl]-ethyl 3-(4-chlorobenzoyl)-2-methyl-benzenehexanoate hydrochloride Using the procedure of Example 2, 3-(4-chlorobenzoyl)-2-methylbenzene hexanoic acid was reacted with thionyl chloride to form 3-(4-chlorobenzoyl)-2-methyl-benzenehexanoic acid chloride which was then reacted with 4-(3-trifluoromethylphenyl)-1-piperazinyl-ethanol followed by hydrochloric acid to obtain 2-[4-(3-trifluoromethylphenyl)-1-piperazinyl]-ethyl 3-(4-chlorobenzoyl)-2-methyl-benzenehexanoate hydrochloride melting at 108° C.

EXAMPLE 4

2-[4-(4-chlorophenyl)-1-piperazinyl]-ethyl 3-(4-chlorobenzoyl)-benzeneacetate hydrochloride Using the procedure of Example 2, 3-(4-chlorobenzoyl)-benzeneacetic acid chloride was reacted with 4-(4chlorophenyl)-1-piperazinyl-ethanol to obtain 2-[4-(4-chlorophenyl)-1-piperazinyl]-ethyl 3-(4-chlorobenzoyl)-benzeneacetate with an Rf=0.68 (9-1-0.05 benzene-ethyl acetate-triethylamine eluant). Treatment with hydrochloric acid resulted in the formation of the hydrochloride salt melting at 142° C.

EXAMPLE 5

Tablets were prepared containing 50 mg of the product of Example 1 or Example 2 and sufficient excipient of lactose, starch, talc and magnesium stearate to obtain a final weight of 350 mg.

PHARMACOLOGICAL DATA

Analgesic Activity

The analgesic activity was determined by the method of Koster et al [Fed. Proc., Vol. 18 (1959), p. 412] using an intraperitoneal injection of acetic acid in mice to provoke repeated stretching and twisting movements for at least 6 hours. Analgesics prevent or diminish these syndromes which are considered to be exteriorization of a diffuse abdominal pain. The acetic acid was a 1% solution in water and the dose which showed the syndrome under these conditions was 0.01ml/g or 100 mg/kg of acetic acid. The test products were orally administered 30 minutes before the acetic acid injection and the mice were not given food or drink since the day before the experiment.

The stretchings were observed for each mouse for a period of 15 minutes starting after the injection and the results were expressed as $DA_{50}$, the dose which reduced by 50% the number of stretchings as compared to control mice. The $DA_{50}$ was 3.5 and 5 mg/kg for the products of Examples 1 and 2, respectively.

Various modifications of the products and process of the invention may be made without departing from the spirit or scope thereof and it is to be understood that the invention is intended to be limited only as defined in the appended claims.

We claim:

1. A compound selected from the group consisting of a compound of the formula

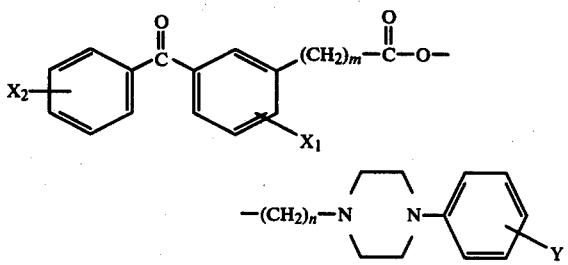

wherein $X_1$ is selected from the group consisting of hydrogen and alkyl of 1 to 5 carbon atoms, $X_2$ is selected from the group consisting of hydrogen, halogen and alkoxy of 1 to 5 carbon atoms, m is a whole number from 1 to 10, n is a whole number from 2 to 5 and Y is in the 2,3 or 4-position and is selected from the group consisting of hydrogen, halogen, $CF_3$—, $CF_3O$—, $CF_3S$—, alkyl of 1 to 8 carbon atoms and alkoxy of 1 to 8 carbon atoms and their non-toxic, pharmaceutically acceptable acid addition salts.

2. A compound of claim 1 wherein $X_2$ is hydrogen.
3. A compound of claim 1 wherein $X_2$ is halogen.
4. A compound of claim 1 wherein $X_2$ is chlorine.
5. A compound of claim 1 wherein $X_1$ is hydrogen.
6. A compound of claim 1 wherein $X_1$ is alkyl of 1 to 5 carbon atoms.
7. A compound of claim 1 wherein $X_1$ is methyl.
8. A compound of claim 1 wherein m is 1.
9. A compound of claim 1 wherein n is 2.
10. A compound of claim 1 wherein Y is —$CF_3$.
11. A compound of claim 1 selected from the group consisting of 2-/4-(3-trifluoromethylphenyl)-1-piperazinyl/-ethyl 3-(4-chlorobenzoyl)-2-methyl-benzeneacetate and its non-toxic, pharmaceutically acceptable acid addition salts.
12. A compound of claim 1 selected from the group consisting of 2-[4-(3-trifluoromethylphenyl)-1-piperazinyl]-ethyl 3-(4-chlorobenzoyl)-benzeneacetate and its non-toxic, pharmaceutically acceptable acid addition salts.
13. A compound of claim 1 selected from the group consisting of 2-[4-(3-trifluoromethylphenyl)-1-piperazinyl]-ethyl 3-(4-chlorobenzoyl)-2-methyl-benzenehexanoate and its non-toxic, pharmaceutically acceptable acid addition salts.
14. A compound of claim 1 selected from the group consisting of 2-[4-(4-chlorophenyl)-1-piperazinyl]-ethyl 3-(4-chlorobenzoyl)-benzeneacetate and its non-toxic, pharmaceutically acceptable acid addition salts.
15. An analgesic composition comprising an analgesically effective amount of at least one compound of claim 1 and an inert pharmaceutical carrier.
16. A composition of claim 15 wherein the compound is selected from the group consisting of 2-[4-(3-trifluoromethyl-phenyl)-1-piperazinyl]-ethyl 3-(4-chlorobenzoyl)-2-methyl-benzeneacetate, 2-[4-(3-trifluoromethylphenyl)-1-piperazinyl]-ethyl 3-(4-chlorobenzoyl)-benzeneacetate, 2-[4-(3-trifluoromethylphenyl)-1-piperazinyl]-ethyl 3-(4-chlorobenzoyl)-2-methyl-benzenehexanoate and 2-(4-chlorophenyl)-1-piperazinyl]-ethyl 3-(4-chlorobenzoyl)-benzeneacetate and their non-toxic, pharmaceutically acceptable acid addition salts.
17. A method of relieving pain in warm-blooded animals comprising administering to warm-blooded animals an analgesically effective amount of at least one compound of claim 1.
18. The method of claim 17 wherein the compound is selected from the group consisting of 2-[4-(3-trifluoromethylphenyl)-1-piperazinyl]-ethyl 3-(4-chlorobenzoyl)-2-methyl-benzeneacetate, 2-[4-(3-trifluoromethyl-phenyl)-1-piperazinyl]-ethyl 3-(4-chlorobenzoyl)-benzeneacetate, 2-[4-(3-trifluoromethylphenyl)-1-piperazinyl]-ethyl 3-(4-chlorobenzoyl)-2-methylbenzenehexanoate and 2-[4-(4-chlorophenyl)-1-piperazinyl]-ethyl 3-(4-chlorobenzoyl)-benzeneacetate and their non-toxic, pharmaceutically acceptable acid addition salts.
19. The method of claim 17 wherein the compound is selected from the group consisting of 2-[4-(3-trifluoromethylphenyl)-1-piperazinyl]-ethyl 3-(4-chlorobenzoyl)-benzeneacetate and its non-toxic, pharmaceutically acceptable acid addition salts.

* * * * *